(12) United States Patent
Cruz Rodriguez

(10) Patent No.: US 11,987,775 B1
(45) Date of Patent: May 21, 2024

(54) SYSTEMS AND METHODS FOR EXTRACTING THC FROM CANNABIS PLANTS

(71) Applicant: Elidan Dynamic, LLC, Tampa, FL (US)

(72) Inventor: Luis Cruz Rodriguez, Tampa, FL (US)

( * ) Notice: Subject to any disclaimer, the term of this patent is extended or adjusted under 35 U.S.C. 154(b) by 0 days.

(21) Appl. No.: 18/106,318

(22) Filed: Feb. 6, 2023

Related U.S. Application Data

(60) Provisional application No. 63/357,796, filed on Jul. 1, 2022, provisional application No. 63/320,184, filed on Mar. 15, 2022.

(51) Int. Cl.
| | | |
|---|---|---|
| *C12G 3/02* | (2019.01) | |
| *C12H 1/07* | (2006.01) | |
| *C12N 1/16* | (2006.01) | |

(52) U.S. Cl.
CPC .............. *C12G 3/02* (2013.01); *C12H 1/063* (2013.01); *C12N 1/16* (2013.01)

(58) Field of Classification Search
CPC ............. C12G 3/02; C12H 1/063; C12N 1/16
USPC ............................................................. 426/7
See application file for complete search history.

(56) References Cited

U.S. PATENT DOCUMENTS

| | | | |
|---|---|---|---|
| 8,778,418 B2 | 7/2014 | Meer | |
| 9,732,009 B2 * | 8/2017 | Raber | ..................... C07B 63/00 |
| 10,793,498 B2 | 10/2020 | Jansen et al. | |
| 2014/0044807 A1 * | 2/2014 | Bisterfeld Von Meer ................... | A61Q 19/00 426/11 |
| 2017/0145445 A1 | 5/2017 | Bazzana et al. | |
| 2017/0240840 A1 | 8/2017 | Privitera et al. | |
| 2019/0076756 A1 | 3/2019 | Moore | |
| 2019/0281872 A1 | 9/2019 | Cilia | |
| 2020/0318041 A1 | 10/2020 | Bardia | |
| 2021/0062228 A1 | 3/2021 | Tengler | |
| 2021/0147770 A1 | 5/2021 | Wendschuh | |
| 2021/0189444 A1 | 6/2021 | Alviar et al. | |

FOREIGN PATENT DOCUMENTS

WO    WO-2008052629 A1 *   5/2008   .............. C12P 13/02

* cited by examiner

*Primary Examiner* — Hamid R Badr
(74) *Attorney, Agent, or Firm* — Bold IP, PLLC

(57) ABSTRACT

A method for extracting THC from cannabis plants. The method includes sorting different parts of a plant and placing each part of the plant along with fermentation materials in a set of fermentation tanks, with the cannabis flowers in the first fermentation tank. Each fermentation tank includes a pair of screen filters and is connected to at least one of the other fermentation tanks above the pair of screen filters and below the pair of screen filters. The method further includes adding an activated yeast to the fermentation tanks on day 0 and leaving the mixtures for 10 days and equalizing the contents of the fermentation tanks on day 10. The method also includes creating a water/sugar mixture and adding 1/10th of the water/sugar mixture to the fermentation tanks each day for 10 days and collecting the macerated oil on day 21 and collecting the infused alcohol on day 21.

20 Claims, 17 Drawing Sheets

FIG. 8

```
===============================================
                     Area Percent Report
===============================================

Sorted By          : Signal
Calib. Data Modified : 17 November, 2021 3:55:05 PM
Multiplier         : 4.300000000e-3
Dilution           : 1.0000
Do not use Multiplier & Dilution Factor with ISTDs Signal 1 : DAD1 D, Sig=230,4 Ref=360,100

Peak  Ret Time Type  Width    Area        Area
 #     [min]         [min]    [mAU*S]      %
----|---------|-----|--------|-----------|------
  1   5.439          0.0000     0.00000   0.00
  2   5.552   BB     0.0489   164.27214   1.58
  3   5.957   BV E   0.0522    15.25307   0.14
  4   6.100   VV R   0.0477  9926.49512  95.57
  5   6.313   VV E   0.0464    23.19101   0.27
  6   6.378   VB E   0.0718    24.14782   0.27
  7   6.430          0.0000     0.00000   0.00
  8   6.810   VB     0.0000     0.00000   0.00
  9   7.382   BB     0.0614   179.40504   1.72
 10   7.947   BB     0.0634    35.04816   0.32
 11   9.042          0.0618    18.11417   0.17

Jacana HPLC 17-Nov-21 4:29:55 PM SYSTEM
```

Data File C:\Users\P...NERAL 2021-11-15 18-59-13\
Sample Name: Sample 20- B5 11-15-21 (Oil)

```
Peak  Ret Time Type  Width    Area        Area
 #     [min]         [min]    [mAU*S]      %
----|---------|-----|--------|-----------|------
Totals:                      1.03859e4  100.00
```

3. Warnings or Errors :

Warning : Calibration warnings (see calibration)
Warning : Calibrated compound(s) not found
Warning : Negative results set to zero (cal.)

```
===============================================
                     *** End of Report ***
```

FIG. 10

Kaycha LABS
10427 Cogdill Road, Suite 500
Knoxville, TN, 37932, US
DEA Number: RK0595249

Certificate of Analysis

Jun 08, 2022 | Canamo
Miami, FL, 33165, US

Kaycha Labs
CBD Resin
N/A

Matrix: Derivative

Sample:KN20607009-003
Harvest/Lot ID: 1
Batch#:1
Seed to Sale# N/A
Batch Date: N/A
Sample Size Received: 3gram
Total Batch Size: N/A
Retail Product Size: 1 gram
Ordered: 06/02/22
Sampled: 06/02/22
Completed: 06/08/22
Sampling Method: N/A

PASSED

Page 1 of 1

| Resin Cannabinoid | Concentration % | Purity % |
|---|---|---|
| THC | 0.0146 | 4.44 |
| CBD | 0.2339 | 71.20 |
| Others(CBG+CBC) | 0.08 | 24.35 |
| Total | 0.3285 | 100 |

FIG. 14

```
===================================================
              Area Percent Report
===================================================

Sorted By          : Signal
Calib. Data Modified : 17 November, 2021 3:55:05 PM
Multiplier         : 4.300000000e-3
Dilution           : 1.0000
Do not use Multiplier & Dilution Factor with ISTDs Signal 1 : DAD1 D, Sig=230,4 Ref=360,100
```

| Peak # | Ret Time [min] | Type | Width [min] | Area [mAU*S] | Area % | Name |
|---|---|---|---|---|---|---|
| 1 | 5.439 |    | 0.0000 | 0.00000 | 0.0000 | CBDV |
| 2 | 5.625 |    | 0.0000 | 0.00000 | 0.0000 | CBDVA |
| 3 | 5.935 |    | 0.0000 | 0.00000 | 0.0000 | CBG |
| 4 | 6.100 | BB | 0.0378 | 6.16676 | 6.4761 | CBD |
| 5 | 6.222 | BB | 0.0427 | 8.36441 | 8.7840 | CBDA |
| 6 | 6.356 |    | 0.0000 | 0.00000 | 0.0000 | CBGA |
| 7 | 6.430 |    | 0.0000 | 0.00000 | 0.0000 | THCV |
| 8 | 6.810 |    | 0.0000 | 0.00000 | 0.0000 | CBN |
| 9 | 7.376 | BB | 0.0608 | 67.77142 | 71.1712 | THC |
| 10 | 7.950 |   | 0.0000 | 0.00000 | 0.0000 | CBC |
| 11 | 9.036 | BB | 0.0602 | 12.92054 | 13.5687 | THCA |

Jacana HPLC 17-Nov-21 3:56:43 PM SYSTEM

FIG. 18

SYSTEMS AND METHODS FOR EXTRACTING THC FROM CANNABIS PLANTS

CROSS-REFERENCE TO RELATED APPLICATIONS

This application is a non-provisional application which claims priority to U.S. Provisional Patent Application No. 63/320,184 filed on Mar. 15, 2022, which is incorporated by reference in its entirety.

This application is a non-provisional application which claims priority to U.S. Provisional Patent Application No. 63/357,796 filed on Jul. 1, 2022, which is incorporated by reference in its entirety.

FIELD OF THE DISCLOSURE

This present disclosure generally relates to the extraction of aromatic oils from plant biomass.

BACKGROUND

Current methods for extracting molecules of THC from cannabis plants are deficient for several reasons. For example, these methods use chemicals to extract these compounds. Because no process will completely remove these chemicals, they will be present in the final product. For some chemicals, this means that the extracted oil cannot be used in some desired applications, such as food additives.

In addition, these methods only use a part of the plant. This is because oil of THC is only found in recoverable amounts in the flowers of the cannabis plants. However, just because the concentration is higher in the flowers, that does not mean that molecules of THC is not present in other portions of the cannabis plant.

Further, these processes are high maintenance and the equipment is expensive. This prevents innovation as the high cost of the equipment and the high amount of maintenance means that the cost barrier to entry is high. Because of these problems, the cost of extracting oil of THC is quite high.

Accordingly, there is a need in the art for a process which allows extraction of molecules of THC without contamination. Further, there is need in the art for the process to have a lower production cost. Finally, there is a need in the art for the process to use all parts of the plant.

BRIEF SUMMARY OF SOME EXAMPLE EMBODIMENTS

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

One example embodiment includes a method for extracting THC from cannabis plants. The method includes sorting different parts of a cannabis plants, wherein the different parts of the cannabis plants include at least flowers and shredding each of the different parts of the plant and placing each part of the plant in a separate container. The method also includes mixing fermentation materials with each of the different parts of the plant and placing the mixed components in a set of fermentation tanks, where each different part of the plant is placed in a separate fermentation tank. Each fermentation tank includes a pair of screen filters, is connected to at least one of the other fermentation tanks at a location above the pair of screen filters and is connected to at least one of the other fermentation tanks at a location below the pair of screen filters. The method further includes activating a yeast mixture and adding the activated yeast mixture to the fermentation tanks on day 0. The method additionally includes leaving the mixtures in each fermentation tank for 10 days to allow fermentation to proceed and equalizing the fermentation tanks on days 0 through 10 by opening the connections between fermentation tanks below the pair of screen filters. The method also includes creating a water/sugar mixture and adding 1/10th of the water/sugar mixture to the fermentation tanks each day for 10 days and collecting the macerated oil on day 21 by allowing the macerated oil to flow to an oil collection tank. The method further includes collecting the infused alcohol on day 21 after collecting the macerated oil by allowing the infused alcohol to flow to an alcohol collection tank.

Another example embodiment includes a method for extracting THC from cannabis plants. The method includes sorting different parts of a plant. The different parts of the plant include roots, stems, branches, and flowers. The method also includes shredding each of the different parts of the plant and placing each part of the plant in a separate container and adding fermentation materials to each container. The fermentation materials include vegetable oil, sugar, and rice. The method further includes placing the mixed components in fermentation tanks. The flowers are placed in a first fermentation tank, the roots, stems, branches, and leaves are placed in a second fermentation tank. Each fermentation tank includes a pair of metallic screen filters is connected to the other fermentation tanks at a location above the pair of metallic screen filters and is connected to the other fermentation tanks at a location below the pair of metallic screen filters. The method additionally includes activating a yeast mixture and adding the activated yeast mixture to the fermentation tanks on day 0. The method moreover includes leaving the mixtures in each fermentation tank for 10 days to allow fermentation to proceed and equalizing the fermentation tanks on days 0 through 10 by opening the connections between fermentation tanks. The method also includes creating a water/sugar mixture and adding 1/10th of the water/sugar mixture to the fermentation tanks each day on days 10-19 and collecting the macerated oil on day 21 by allowing the macerated oil to flow to an oil collection tank. The method further includes collecting the infused alcohol on day 21 after collecting the macerated oil by allowing the infused alcohol to flow to an alcohol collection tank.

Another example embodiment includes a system for extracting THC from cannabis plants. The system includes a first fermentation tank. The first fermentation tank includes a first screen filter, where the first screen filter is located approximately 25% of total height of the first fermentation tank from the top of the first fermentation tank. The first fermentation tanks also includes a second screen filter, where the second screen filter in the pair of metallic screen filters is located approximately 25% of total height of the first fermentation tank from the bottom of the first fermentation tank. The first fermentation tank is configured to receive the flowers of cannabis plants between the first screen filter and the second screen filter. The system further includes a second fermentation tank. The second fermentation tank includes a first screen filter, where the first screen filter is located approximately 25% of total height of the second fermentation tank from the top of the second fermentation tank. The second fermentation tank also includes a second screen filter, where the second screen filter in the pair of metallic screen filters is located approximately 25% of total height of the second fermentation tank from the bottom of the second fermentation tank. The second fermentation tank further includes a first connection to the first fermentation tank above the first screen filter and a second connection to the first fermentation tank below the second screen filter. The second fermentation tank is configured to receive the roots, stems, branches, and leaves of the cannabis plants between the first screen filter and the second screen filter. The system additionally includes a third fermentation tank. The third fermentation tank includes a first screen filter, where the first screen filter is located approximately 25% of total height of the third fermentation tank from the top of the third fermentation tank. The third fermentation tank also includes a second screen filter, where the second screen filter in the pair of metallic screen filters is located approximately 25% of total height of the third fermentation tank from the bottom of the third fermentation tank. The third fermentation tank further includes a first connection to the first fermentation tank above the first screen filter and a second connection to the first fermentation tank below the second screen filter. The third fermentation tank is configured to receive the roots, stems, branches, and leaves of the cannabis plants between the first screen filter and the third screen filter. The system moreover includes a fourth fermentation tank. The fourth fermentation tank includes a first screen filter, where the first screen filter is located approximately 25% of total height of the fourth fermentation tank from the top of the fourth fermentation tank. The fourth fermentation tank also includes a second screen filter, where the second screen filter in the pair of metallic screen filters is located approximately 25% of total height of the fourth fermentation tank from the bottom of the fourth fermentation tank. The fourth fermentation tank also includes a first connection to the first fermentation tank above the first screen filter and a second connection to the first fermentation tank below the second screen filter. The fourth fermentation tank is configured to receive the roots, stems, branches, and leaves of the cannabis plants between the first screen filter and the fourth screen filter. The system also includes a storage tank, where the storage tank includes a connection to the first fermentation tank and a macerated oil tank, where the macerated oil tank includes a connection to the fourth fermentation tank above the first screen filter of the fourth fermentation tank. The system further includes an infused alcohol tank, where the infused alcohol tank includes a connection the to the fourth fermentation tank below the second screen filter of the fourth fermentation tank.

These and other objects and features of the present invention will become more fully apparent from the following description and appended claims or may be learned by the practice of the invention as set forth hereinafter.

BRIEF DESCRIPTION OF THE DRAWINGS

The preceding and following embodiments and descriptions are for illustrative purposes only and are not intended to limit the scope of this disclosure. Other aspects and advantages of this disclosure will become apparent from the following detailed description.

Embodiments of the present disclosure are described in detail below with reference to the following drawings. These and other features, aspects, and advantages of the present disclosure will become better understood with regard to the following description, appended claims, and accompanying drawings. The drawings described herein are for illustrative purposes only of selected embodiments and not all possible implementations and are not intended to limit the scope of the present disclosure.

Figure 1:
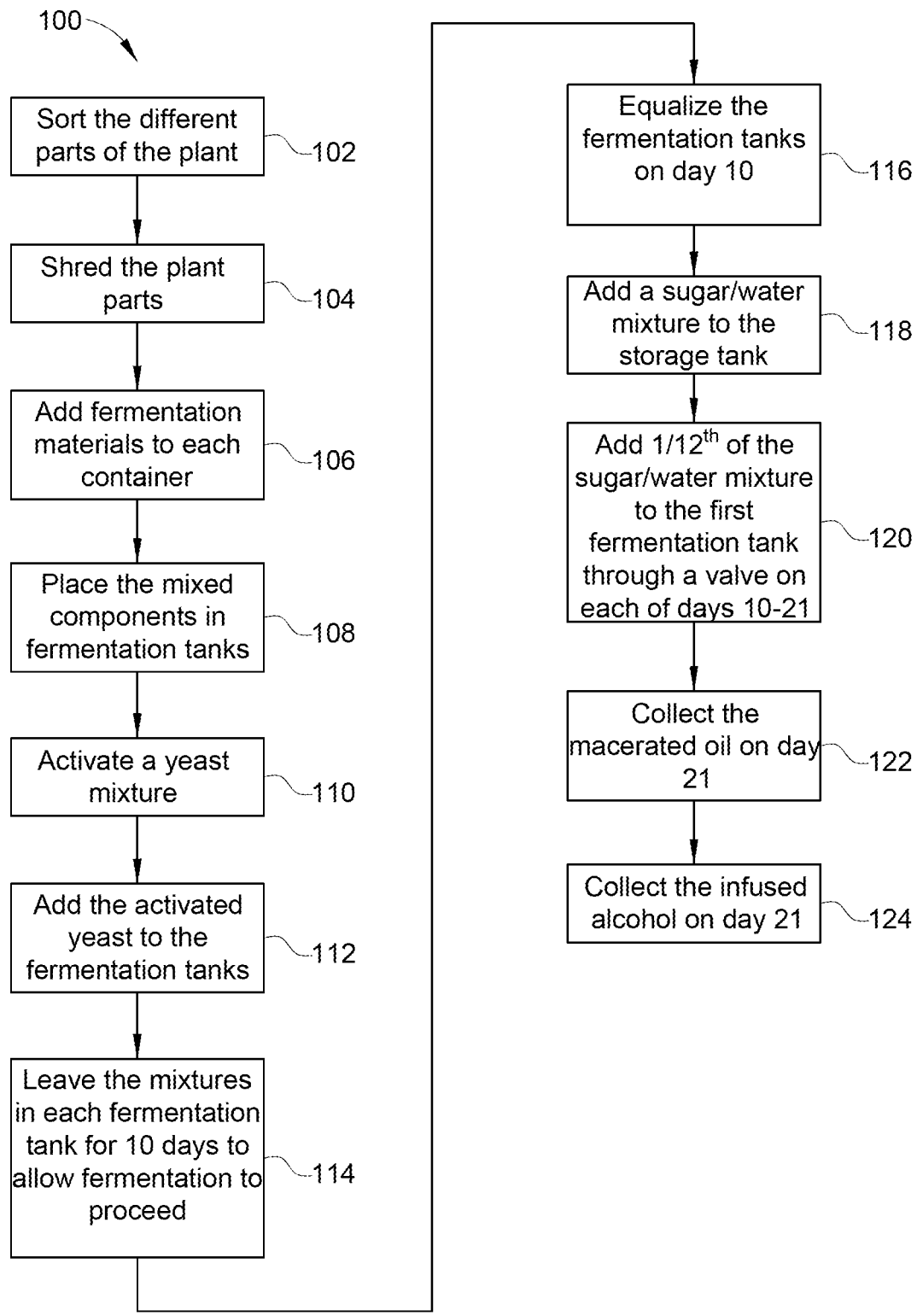
Figure 2:
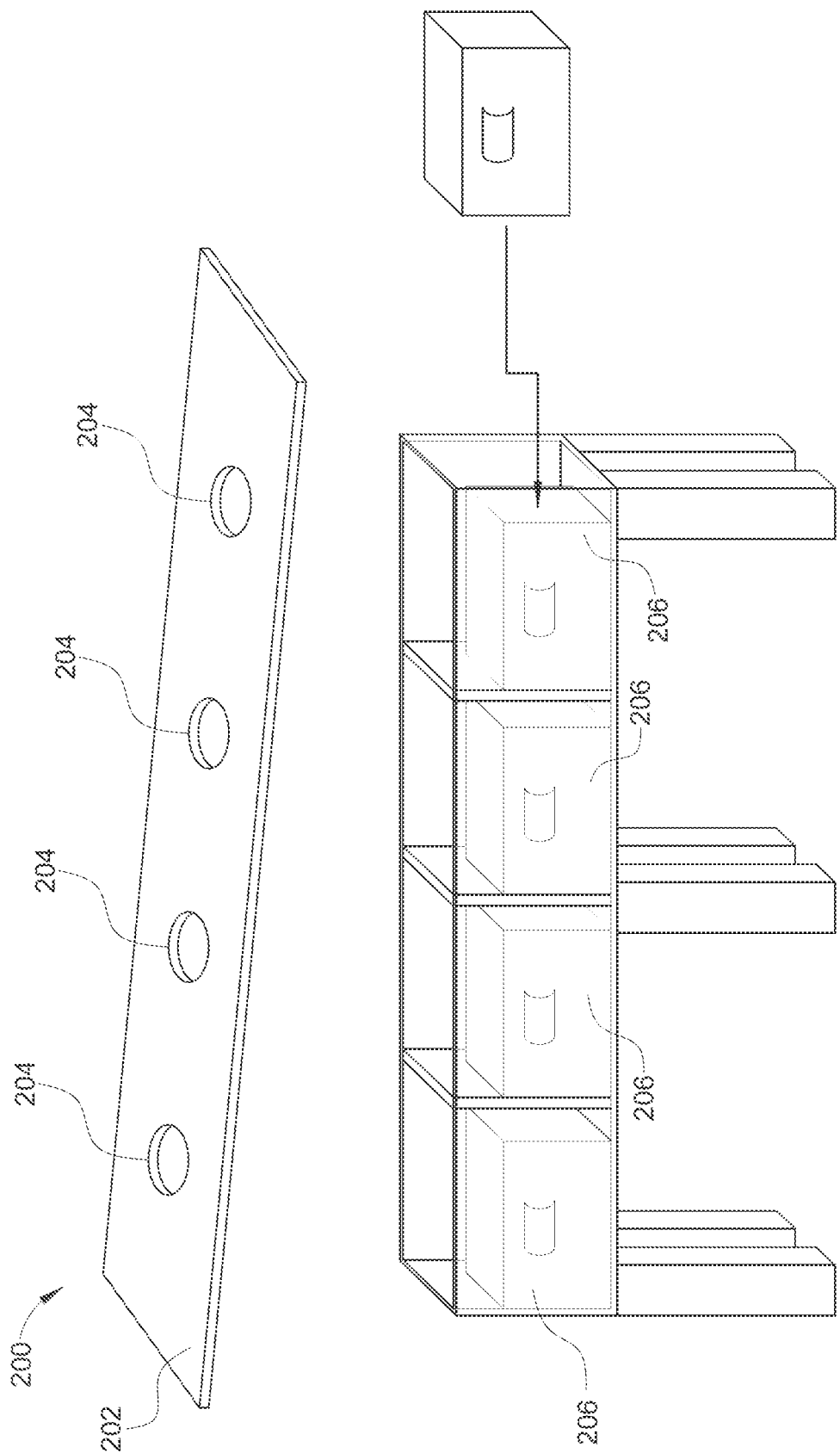
Figure 3:
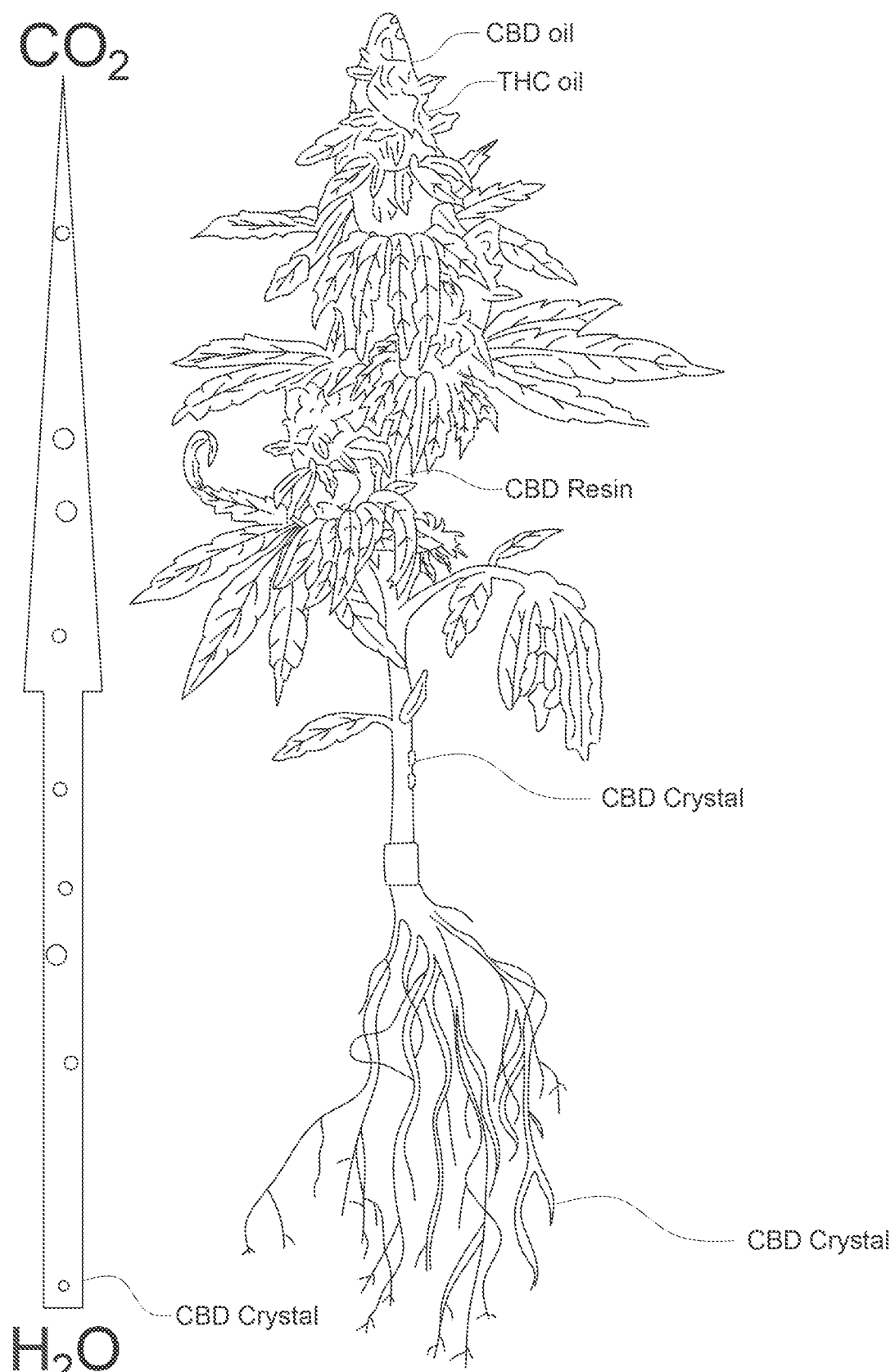
Figure 4:
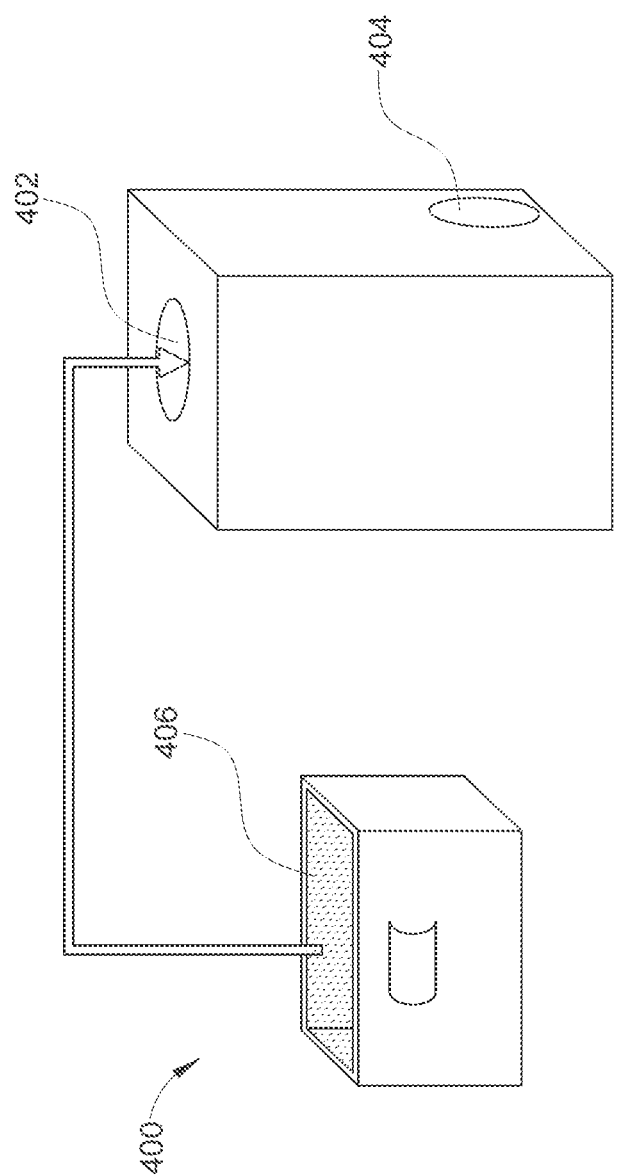
Figure 5:
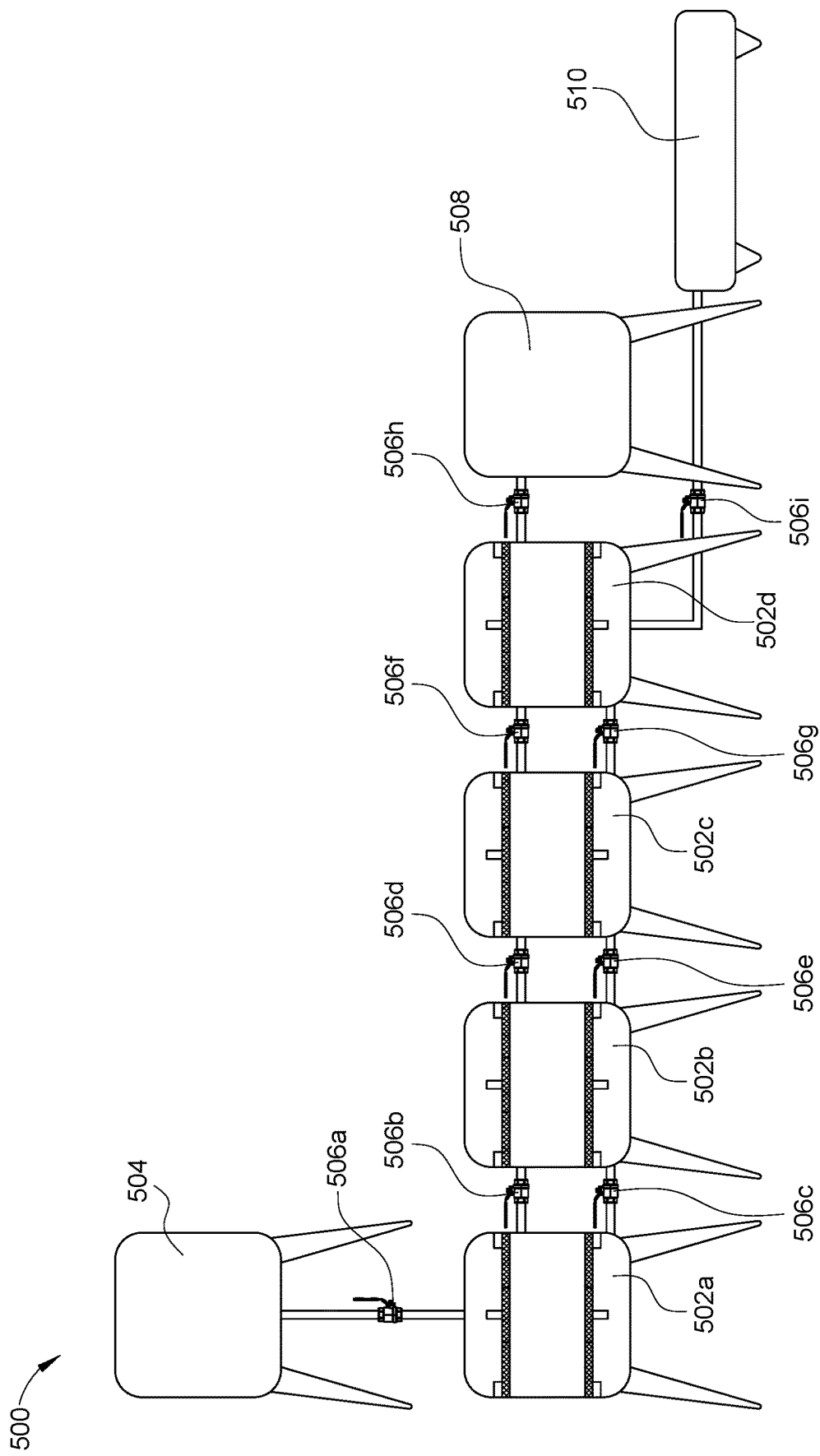
Figure 6:
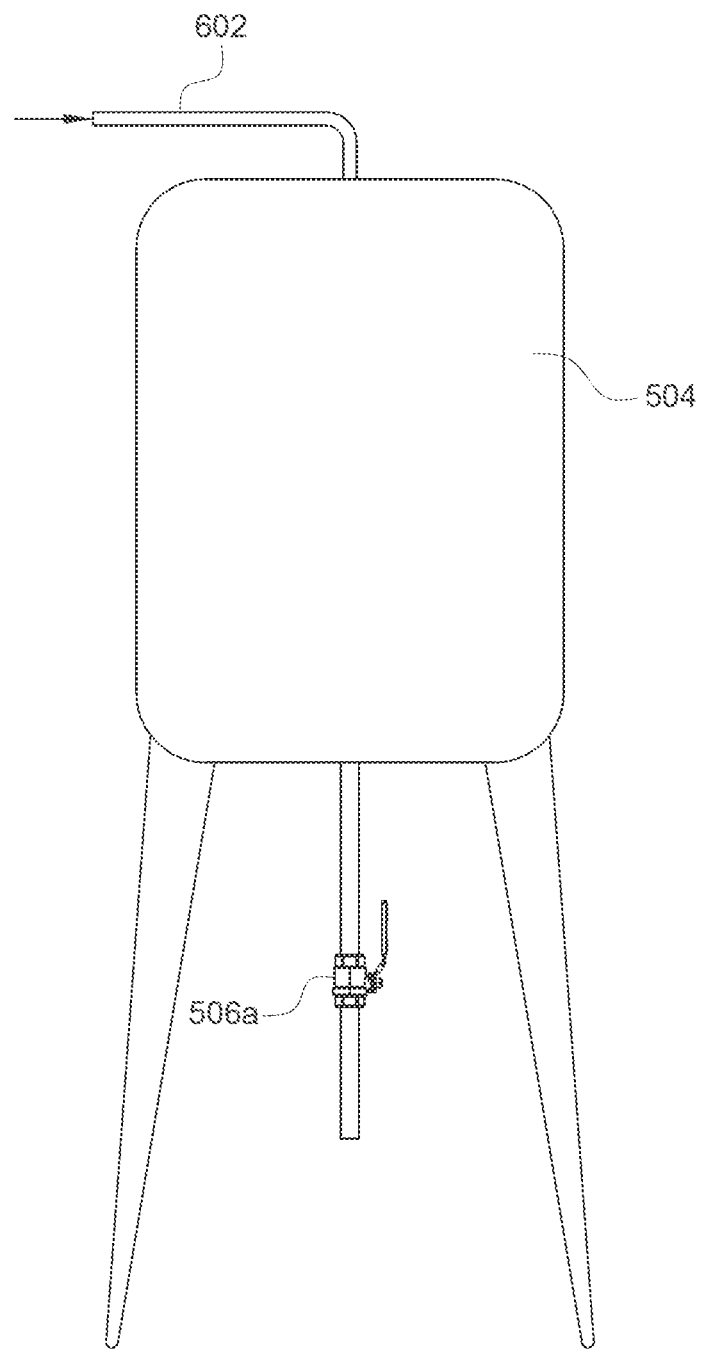
Figure 7:
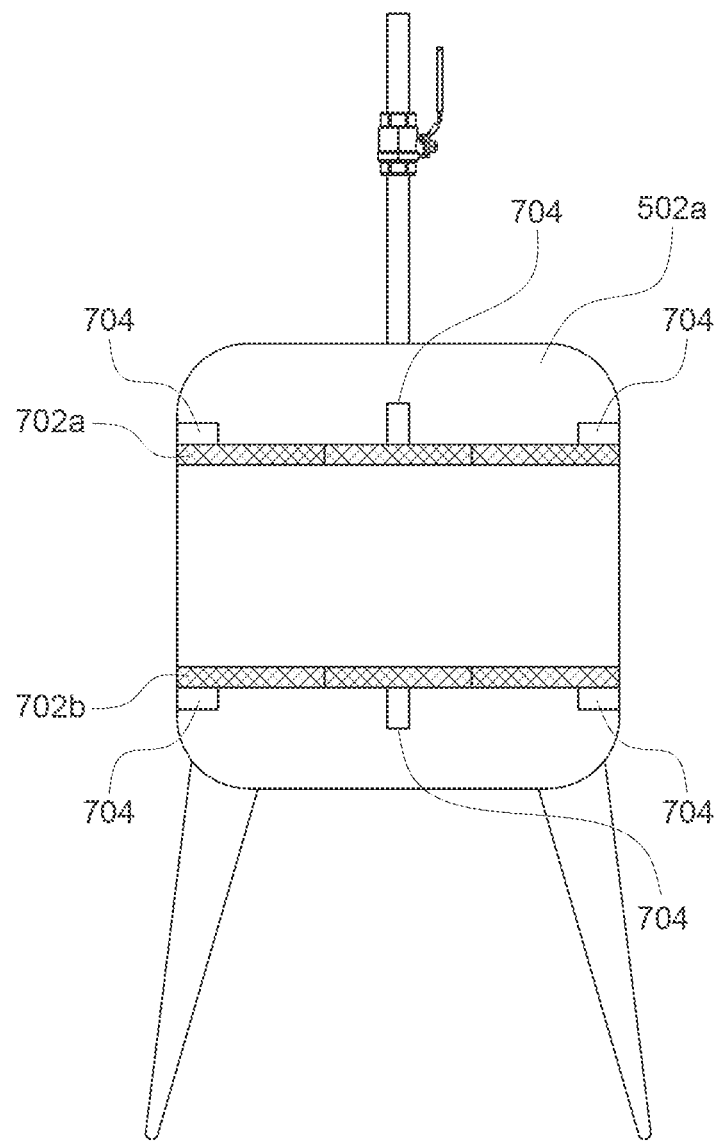
Figure 9:
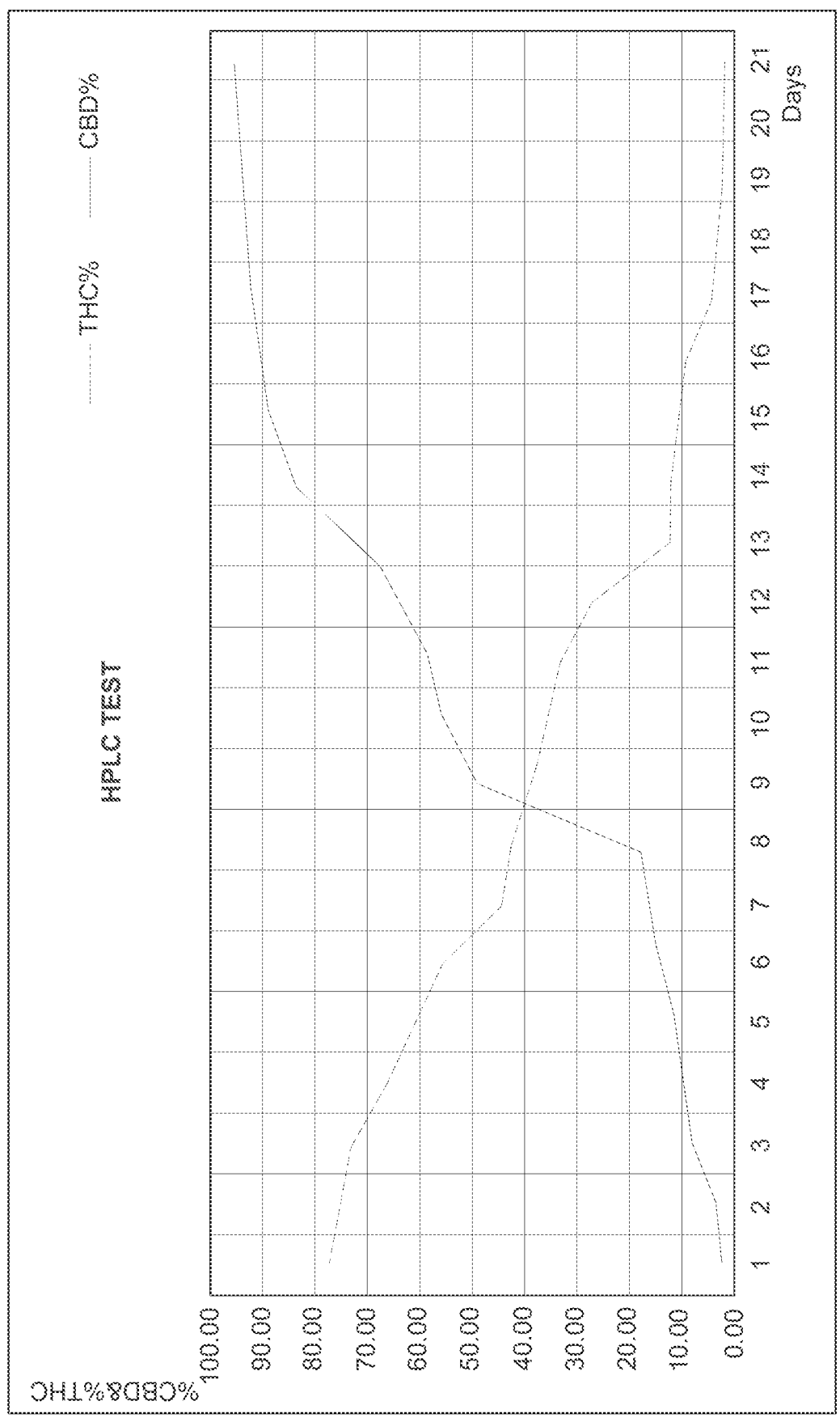
Figure 11:
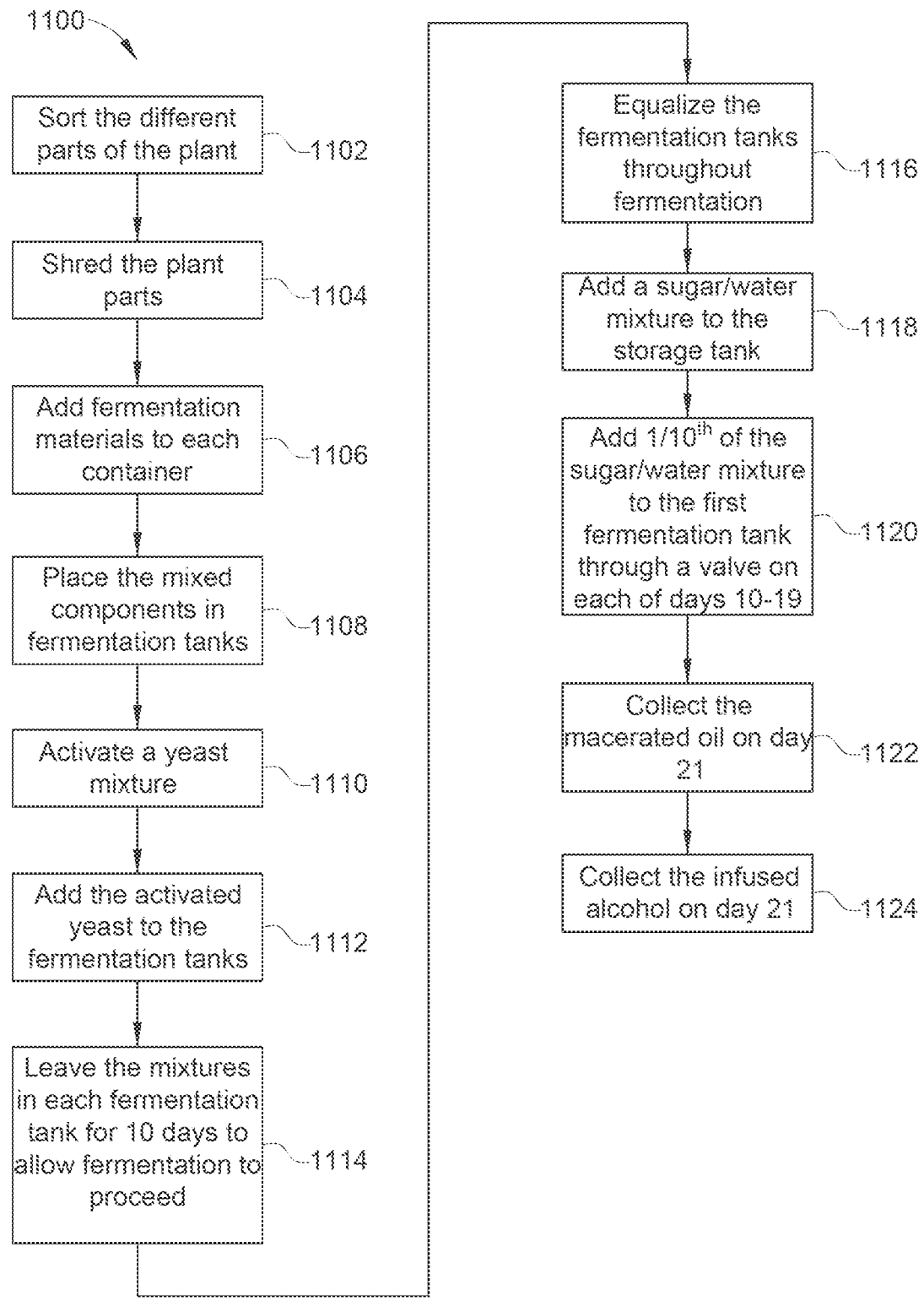
Figure 12:
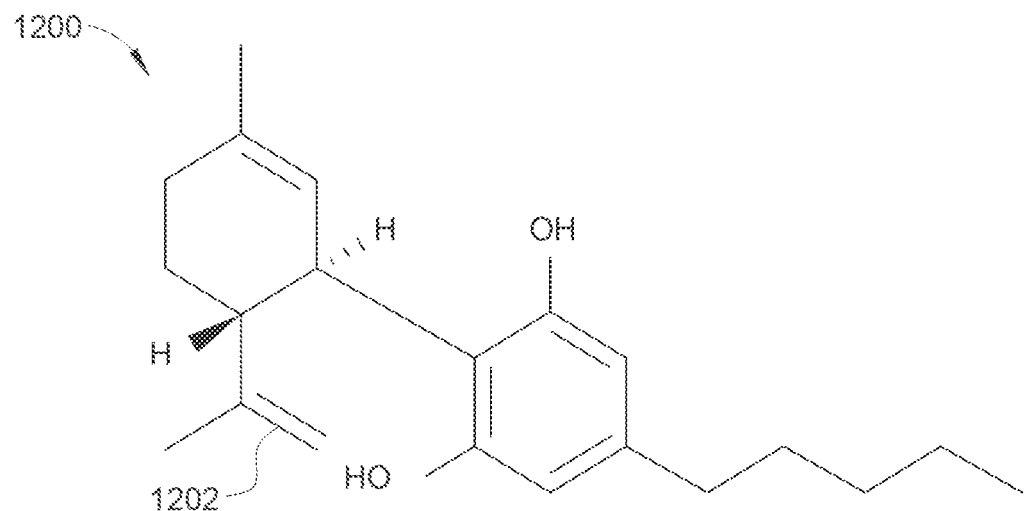
Figure 13:
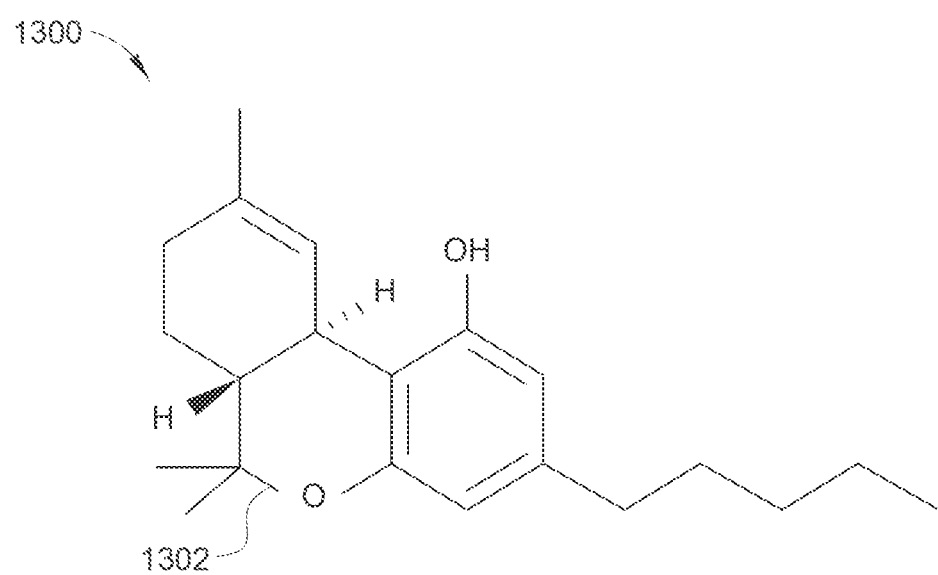
Figure 15:
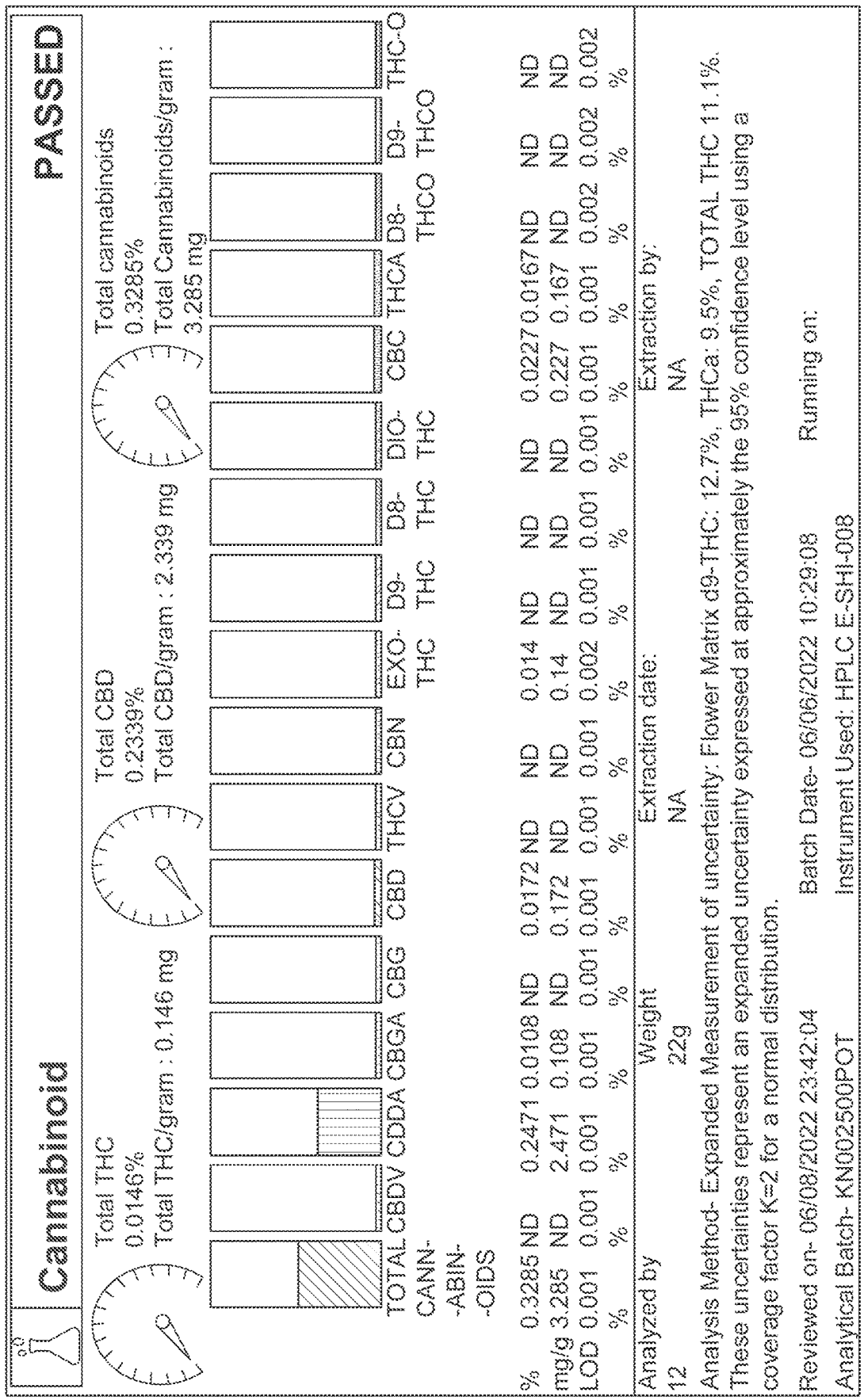
Figure 16:
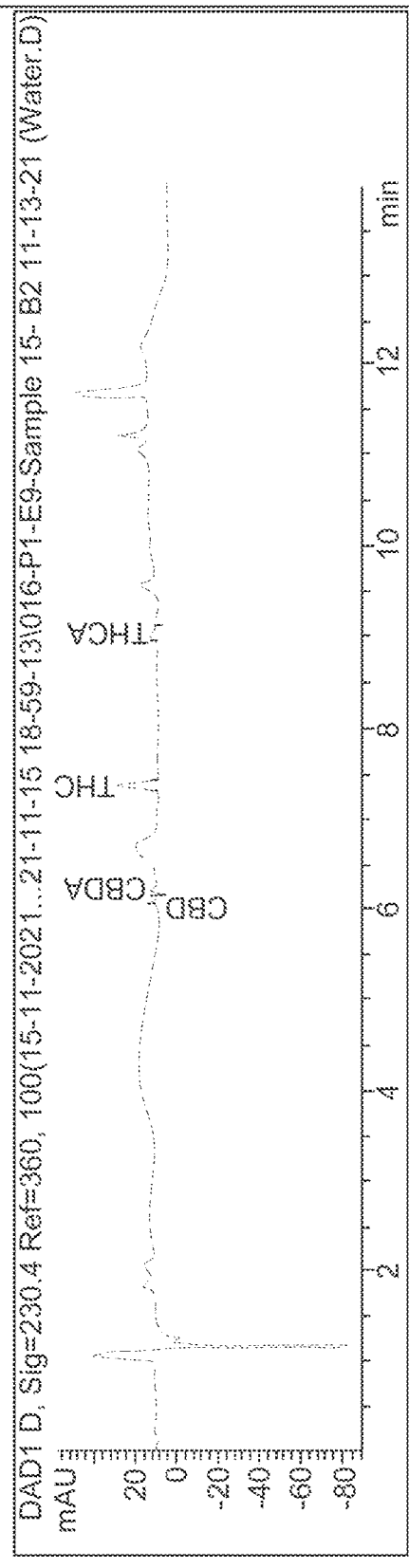
Figure 17:
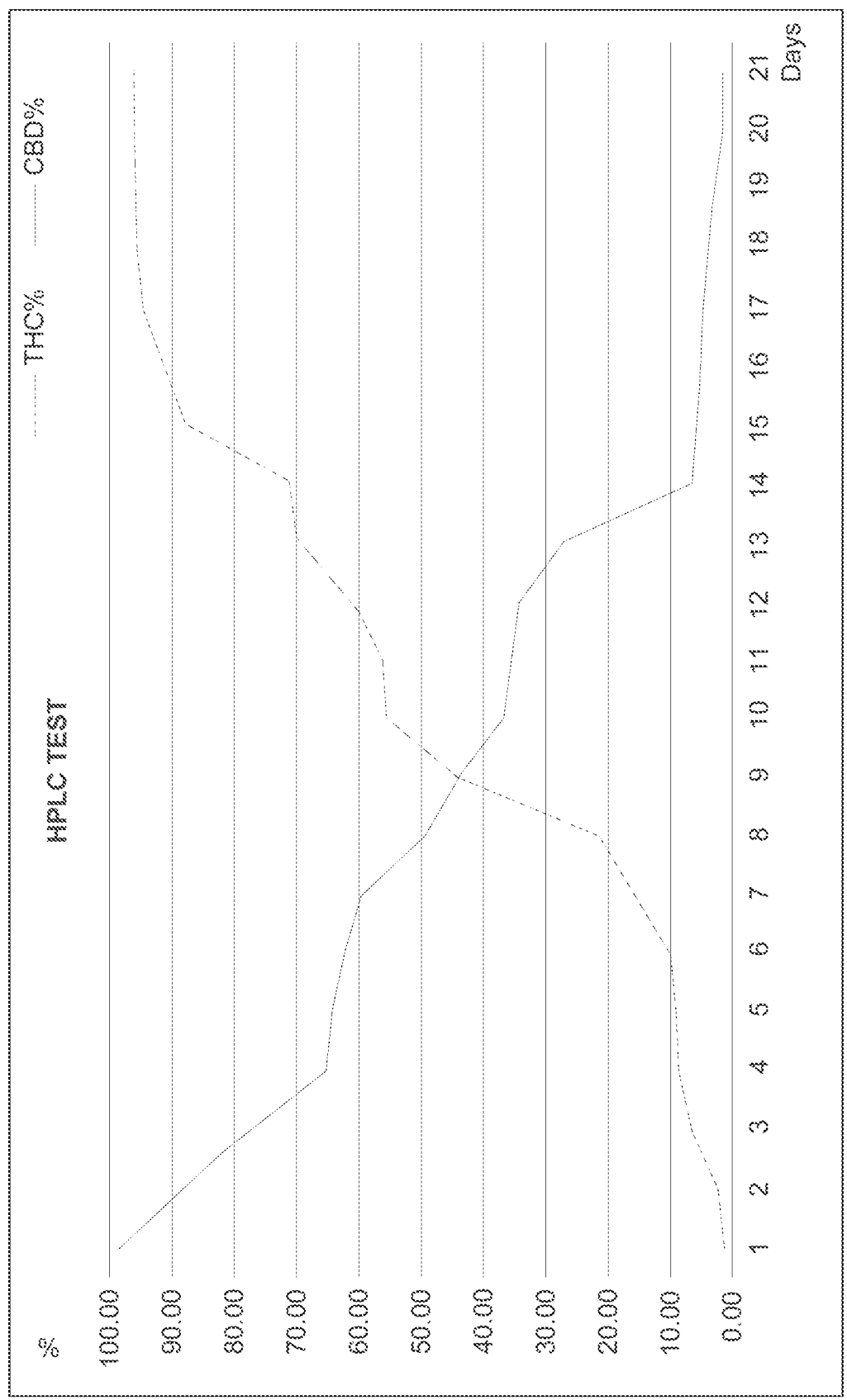

To further clarify various aspects of some example embodiments of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 1 is a flow chart illustrating a method for extracting aromatic oils;

FIG. 2 illustrates an example sorting table that can be used to sort the different parts of a cannabis plant;

FIG. 3 illustrates the location of CBD and THC in a cannabis plant;

FIG. 4 illustrates an example of a mulching machine that can be used for the comminution of the plant matter;

FIG. 5 shows an example of a system which can be used for fermentation;

FIG. 6 illustrates a more detailed example of storage tank 504 from FIG. 5;

FIG. 7 illustrates an example of a fermentation tank;

Figure 8:
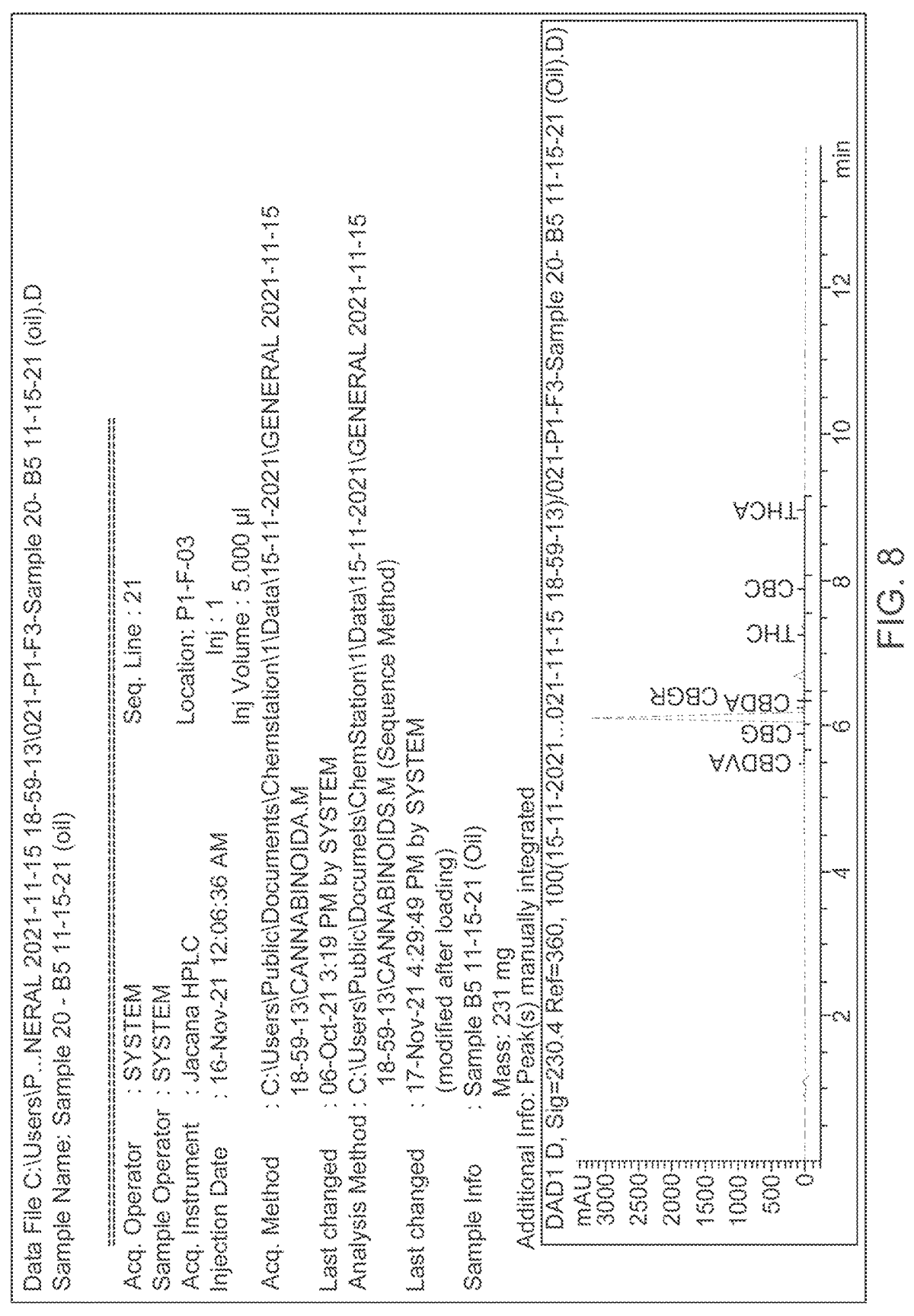

FIG. 8 illustrates an example of a high performance liquid chromatography (HPLC) sample report of a sample extracted by the disclosed method showing percentage of CBDV, CBDVA, CBG, CBD, CBDA, CBGA, THCV, CBN, THC, CBC, THCA;

FIG. 9 illustrates an example line graph of HPLC results over a period of 21 days of fermentation;

FIG. 10 illustrates the HPLC results on day 21;

FIG. 11 is a flow chart illustrating a method for extracting THC oils;

FIG. 12 illustrates a 2D structural drawing of CBD;

FIG. 13 illustrates a 2D structural drawing of THC;

FIG. 14 illustrates the percentage of various Cannabinoids (including CBD and THC) prior to transformation of CBD into THC;

FIG. 15 illustrates the same results, but as a percentage within the fermented alcohol and macerated oil;

FIG. 16 illustrates an example of a high performance liquid chromatography (HPLC) sample report of a sample extracted by the disclosed method showing percentage of CBD, CBDA, THC, and THCA;

FIG. 17 illustrates an example of high performance liquid chromatography (HPLC) during the 21 days of fermentation; and FIG. 18 illustrates the HPLC results on day 21 including percentages of cannabinoids: CBDV, CBDVA, CBG, CBD, CBDA, CBGA, THCV, CBN, THC, CBC, and THCA.

DETAILED DESCRIPTION

The present description relates to a method for extracting aromatic oils. The disclosed method is cheaper and requires less capital investment than current methods. In addition, the disclosed method results in a higher concentration of the desired aromatic oils.

Reference will now be made to the figures wherein like structures will be provided with like reference designations. It is understood that the figures are diagrammatic and schematic representations of some embodiments of the invention, and are not limiting of the present invention, nor are they necessarily drawn to scale.

FIG. 1 is a flow chart illustrating a method 100 for extracting aromatic oils. The method 100 results in a macerated oil by using fermentation of an entire plant, rather than only a portion of a plant. The method 100 can be used to extract any aromatic oils, including essential oils. Fragrance oils, also known as aroma oils, aromatic oils, and flavor oils are blended synthetic aroma compounds or natural essential oils that are diluted with a carrier like propylene glycol, vegetable oil, or mineral oil. Aromatic oils are used in a variety of applications, including perfumery, cosmetics, and flavoring of food. Cannabidiol ("CBD") and Tetrahydrocannabinol ("THC") extraction from cannabis plants will be used as exemplary herein, but one of skill in the art will appreciate that the method can be used for any desired aromatic oil. The method 100 can produce CBD at much higher rates and lower costs than conventional methods. For example, this method can produce CBD at a cost of about $20 per liter versus a current cost of about $2,000 per liter. The CBD produced by the method will be sold under the name "ELIDANLORD" which is being registered under TM serial no. 97558693.

FIG. 1 shows that the method 100 can include sorting 102 the different parts of the plant. The different parts of a cannabis plant have different chemical properties and have compounds such as CBD and THC in different concentrations and at different stages of chemical creation, so sorting allows CBD and THC to be extracted differently. To sort the parts of the plant, the cannabis plant is uprooted and washed. The plant is then mechanically comminuted (e.g., cutting or grinding) and the different plant parts are placed in different containers, which can be labeled (for example, with the part of the plant, the date of sorting, etc.).

For example, FIG. 2 illustrates an example of sorting table 200 that can be used to sort the different parts of a cannabis plant. The table 200 allows a worker to begin mechanical comminution of the plant materials. For example, the table 200 can be used to cut up or grind plant materials, which are then categorized by the portion of the plant from which the materials were extracted. For example, the table 200 has a top 202 where the plant can be cut and a series of openings 204 where the plant material can be deposited after it is appropriately sorted. In some embodiments, roots can be placed in the first opening 204, stems in the second opening 204, branches in the third opening 204, and flowers in the fourth opening 204. However, one of skill in the art will appreciate that which part of the plant goes into which opening does not matter if the placement is consistent. A series of baskets 206 are placed under the openings 204 to catch the sorted plant material.

The different parts of a cannabis plant have different chemical properties and have compounds such as CBD and THC in different quantities and at different stages of chemical creation, so sorting allows them to be extracted differently. As shown in FIG. 3, CBD within a cannabis plant begins as crystals in the root system of the plant. The crystals migrate with water and other materials throughout the plant. For example, the stem has smaller CBD crystals, branches and leaves have CBD resin, and CBD oil is found predominantly in the cannabis flowers. THC, on the other hand, is produced primarily in the cannabis flowers, with some production occurring in the leaves.

FIG. 1 shows that the method 100 can also include shredding 104 of the plant parts. Shredding 104 (or mulching) is further comminution of the plant materials to create much smaller particles. Shredding 104 does not change the volume of the plant materials but does change the surface area. In other words, by mechanically breaking up the plant matter, the surface area available for CBD and THC extraction is increased, decreasing the time needed for the extraction process. The shredded materials can be weighed and labeled similar to the above. Typically, once the amount of biomass is between 3 and 5 kilograms, the container is replaced with a new container, but the amount of biomass depends on the size of fermentation tanks (described below).

FIG. 4 illustrates an example of a mulching machine 400 that can be used for the comminution of the plant matter 406. The plant matter 406 is placed in a first opening 402 where it can enter a chamber with shredders. As the plant matter 406 is shredded, it passes to a second opening 404 where the plant matter 406 can be removed. Removal can include automatic removal, such as the shredded plant material 406 falling into a sack, bin or other container.

FIG. 1 additionally shows that the method 100 can include adding 106 fermentation materials to each container (which already includes the shredded plant matter). The fermentation materials depend on the desired final product. Exemplarily, rice will be used herein, which would result in infused rice wine, but other materials are contemplated herein, such as wine from grapes, wine from grains such as beans and peas, fruit wine, wine from aromatic plants such as garden flowers, carnations, poppies, roses, etc., beer, and other spirits. For the production of rice wine, the fermentation materials can exemplarily include vegetable oil (~1.9 times the cannabis biomass by weight), sugar (~0.25 times the cannabis biomass by weight) and rice (~1.9 times the cannabis biomass by weight). Vegetable oils, or vegetable fats, are oils extracted from seeds or from other parts of fruits. Soybean oil, grape seed oil, and cocoa butter are examples of seed oils or fats from seeds while olive oil, palm oil, and rice bran oil are examples of fats from other parts of fruits.

FIG. 1 moreover shows that the method 100 can include placing 108 the mixed components in fermentation tanks. Each different portion of the plant (e.g., root, stem leaves, flowers) is placed in different fermentation tanks. For example, FIG. 5 shows an example of a system 500 which can be used for fermentation. The system 500 includes a first fermentation tank 502a, a second fermentation tank 502b, a third fermentation tank 502c, and a fourth fermentation tank 502d (collectively "fermentation tanks 502"). By way of example, first fermentation tank 502a corresponds to the fermentation of the root of the plant, second fermentation tank 502b corresponds to the fermentation of the stem of the plant, third fermentation tank 502c corresponds to the fermentation of the branches and leaves of the plant, and fourth fermentation tank 502d corresponds to the fermentation of the flowers of the plant (if it does not have flowers, it is the fermentation of the mixture of roots, stems and leaves or only three fermentation tanks 502 are used). The fermentation tanks are constructed of food grade steel, but other materials are contemplated herein. For example, wooden casks can serve as fermentation tanks 502, which changes the nature of the infused alcohol product.

Although the fermentation tanks 502 are shown sequentially in FIG. 5, any method of connection is contemplated herein. For example, the first fermentation tank 502a can act as a "hub" with the second fermentation tank 502b, third fermentation tank 502c and fourth fermentation tank 504d all directly connected to the first fermentation tank 502a but not directly connected to one another (only indirectly connected through the first fermentation tank 502a). The connection pattern isn't important, but it is important that the fermentation tanks 502 are all connected directly or indirectly to one another.

FIG. 1 also shows that the method 100 can include activating 110 a yeast mixture. Activating 110 the yeast mixture involves adding yeast to a water and sugar mixture which allows the yeast to begin growing and undergoing metabolic processes. Activated yeast begins to work faster than inactive or dry yeast. Activating 110 a yeast mixture involves adding warm water (between 32° C. and 38° C. into storage tank 504 of FIG. 5). Then, sugar at a ratio of approximately 1 to 100 is added (1 kilogram of sugar for every 100 kilograms of water—1 liter of water weighs 1 kilogram) and yeast at a ratio of approximately 1 to 1000 is added (1 gram of yeast for every 1 kilogram of water). The sugar is a food source for the yeast and the warm water increases the speed of yeast metabolic processes. The water/sugar/yeast mixture is left alone for ~45 minutes to incubate. As used in the specification and the claims, the term approximately shall mean that the value is within 10% of the stated value, unless otherwise specified.

FIG. 6 illustrates a more detailed example of storage tank 504 from FIG. 5, showing that the tank has a water intake 602, which can be used to fill the tank. FIG. 6 also shows that valve 506a is a simple valve that allows storage tank 504 to be drained when opened (one of skill in the art will appreciate that the valve 506a can be replaced with a pump, but the pump may damage the activated yeast and can become clogged with yeast, making a gravity operated system preferable but not the only viable option).

FIG. 1 further shows that the method 100 can include adding 112 the activated yeast to the fermentation tanks (this is counted as day 0). This is done by having valves 506b, 506c, 506d, 506e, 506f, 506g, and 506h of FIG. 5 open (valve 506i is closed) and then opening valve 506a, allowing the activated yeast mixture to flow into fermentation tanks 502 (the fluid level will not be high enough to flow into macerated oil tank 508). The cannabis biomass in each fermentation tank 502 is now suspended in the activated yeast mixture.

FIG. 7 illustrates an example of a fermentation tank 502a. The fermentation tank 502a includes a first screen filter 702a and a second screen filter 702b (collectively "screen filters 702"). Screen filters 702 are composed of food grade steel or any other suitable material. The second screen filter 702b is approximately 25% of the height from the bottom of the fermentation tank 502a and the first screen filter 702a is approximately 25% of the height from the top of the fermentation tank 502a. The biomass is placed in the area between the screen filters 702. To prevent the biomass from getting caught on support elements, the first screen filter 702a has supports 704 on the top of the metallic screen filter 702 and the second screen filter 702b has supports 704 on the bottom of metallic screen filter 702. Fermentation tanks 502b, 502c and 502d of FIG. 5 are similar in configuration but have more inputs on the sides and no top input. One of skill in the art will appreciate, however, that each fermentation tank 502 can be the same and just have valves closed or connection ports capped.

FIG. 1 moreover shows that the method 100 includes leaving 114 the mixtures in each fermentation tank for 10 days to allow fermentation to proceed. Because storage tank 504 is the same volume as fermentation tanks 502, the activated yeast mixture will reach to approximately the second screen filter 702b. However, because the biomass mixture includes oil (as part of the fermentation materials) there will be a water/oil interface at or near the second screen filter 702b. The yeast can migrate through the interface and will equalize between the water and the vegetable oil, but the biomass will remain within the vegetable oil. After the volume equalizes in the fermentation tanks, valves 506a, 506b, 506c, 506d, 506e, 506f, 506g, and 506h are closed and fermentation in each of the fermentation tanks 502 proceeds independent of the fermentation in the other fermentation tanks 502 on days 0-10.

One of skill in the art will understand that leaving 114 the fermentation tanks alone means that the addition of other materials (such as additional biomass or activated yeast) does not occur but does not mean that samples and measurements cannot be taken. For example, on each day samples can be taken from each of the fermentation tanks 502. Samples can include 500 mL from each of the fermentation tanks 502. The samples may be tested for pH, temperature, alcoholic %, High-Performance Liquid Chromatography (HPLC), etc. Examples of test results are shown in FIGS. 8, 9 and 10 (where FIG. 8 illustrates an example of a high performance liquid chromatography (HPLC) sample report of a sample extracted by the disclosed method showing percentage of CBDV, CBDVA, CBG, CBD, CBDA, CBGA, THCV, CBN, THC, CBC, THCA; FIG. 9 illustrates an example of high performance liquid chromatography (HPLC) during the 21 days of fermentation; and FIG. 10 illustrates the HPLC results on day 21). Over time, CBD is extracted where it remains in the vegetable oil because it is hydrophobic. THC, on the other hand, is extracted and migrates into the water in the fermentation tanks because it is hydrophilic. Thus, both CBD and THC are extracted but effectively separated. Further, the rice is being fermented creating a rice wine which is infused with THC within the water.

FIG. 1 also shows that the method 100 can include equalizing 116 the fermentation tanks 502 on day 10. Equalizing 116 the fermentation tanks 502 includes opening valves 506b, 506c, 506d, 506e, 506f, 506g, and 506h. This allows the water/sugar/yeast portion of each of the fermentation tanks 502 to mix with one another. Because each fermentation tank 502 has different plant matter (was taken from different parts of the plant), the amounts of CBD and THC will be different in each of the fermentation tanks 502 but will equalize over time thanks to diffusion when the connections are opened.

FIG. 1 further shows that the method 100 can include adding 118 a sugar/water mixture to the storage tank 504. Storage tank 504 is refilled with warm water. Sugar is added to the water in storage tank 504 at a ratio of 1 to 100 (1 kilogram of sugar for every 100 kilograms of water).

FIG. 1 additionally shows that the method 100 can include adding 120 $\frac{1}{12}^{th}$ of the sugar/water mixture to first fermentation tank 502a through valve 506a each day of days 10-21. This raises the level of the water/oil interface in each tank (this interface would be at about 50% the height of each fermentation tank, except the presence of the biomass pushes this higher—closer to 75% of the height of the fermentation tanks). In addition, it raises the top level of the oil within the tank, so that the oil flows through valves 506b, 506d, 506f and 506h into macerated oil tank 508.

FIG. 1 moreover shows that the method 100 can include collecting 122 the macerated oil on day 21. Macerated oils are vegetable oils to which other matter, such as herbs, has been added. Thus, the macerated oil can be, for example, vegetable oil with CBD mixed into the oil. Collecting 122 the macerated oil includes mixing the oil. Because different parts of the plant have different levels of CBD, mixing the oil during collection equalizes the CBD concentration throughout the oil. Collecting 122 the macerated oil may also include closing valve 602h prior to mixing so that oil is not pushed back into fermentation tanks 502 during mixing.

FIG. 1 also shows that the method 100 can include collecting 124 the infused alcohol on day 21. Collecting 124 the infused alcohol includes opening valve 506i. Because valves 506c, 506e, 506g are opened but valves 506b, 506d, 506f, and 506h are closed, any liquid now flows into infused alcohol tank 510 through valve 506i. Because the macerated oil has been removed, the remaining liquid is THC infused alcohol (in this example, rice wine).

The concentrations of CBD in the macerated oil and THC in the infused rice wine can be calculated using the following equations:

$$[CBD] = \frac{\log\left(\frac{V(\text{Passive})}{V(\text{Total})} * \% \text{ Alcohol(final)} * \text{pH(final)} * \frac{\text{Temperature (° C.)}}{\text{number of fermentaion days}}\right)}{\cos\left(\frac{m(\text{BM})}{m(\text{vegetal oil})} - \frac{m(\text{sugar})}{m(\text{rice})}\right)}$$

$$[THC] = \frac{[CBD]}{[\% \text{ Alcohol(final)}] * [\% \text{ Alcohol(final)}]}$$

$$\% [CBD] = [CBD] * 100$$

$$\% [THC] = [THC] * 100$$

$$\text{if, } X = \frac{[THC] + [CBN]}{[CBD]}; \text{ and } [CBN] = 0$$

$$X = \frac{1}{[\% \text{ Alcohol(final)}] \wedge 2}$$

These concentrations are significantly higher than concentrations obtained using conventional methods.

FIG. 11 is a flow chart illustrating a method 1100 for extracting THC oils. The method 1100 results in an infused alcohol by using alcoholic fermentation of an entire cannabis plant, rather than only a portion of the plant. FIG. 11 is similar to FIG. 1 in many respects, however, one of skill in the art will appreciate that there are differences which result in a different product. In particular, the amount of CBD is reduced because the CBD is converted into THC. This is a natural process that occurs within the flowers of a cannabis plant. The cannabis plant produces CBD throughout the plant, and after the CBD migrates to the flower, it is then converted by an enzyme into THC. Thus, the method 1100 can produce THC at much higher rates and lower costs than conventional methods by using this process. The THC produced by the method will be sold under the name "ELIDANLORD" which is being registered under TM serial no. 97558693.

FIG. 12 illustrates a 2D structural drawing of CDB 1200 (IUPAC name 2-[(1R,6R)-6-Isopropenyl-3-methylcyclohex-2-en-1-yl]-5-pentylbenzene-1,3-diol) and FIG. 13 illustrates a 2D structural drawing of THC 1300 (specifically the Delta-9-THC isomer with IUPAC name (6aR,10aR)-6,6,9-Trimethyl-3-pentyl-6a,7,8,10a-tetrahydro-6H-benzo[c]chromen-1-ol and other names which include (6aR,10aR)-delta-9-Tetrahydrocannabinol and (—)-trans-Δ9-Tetrahydrocannabinol). Both CBD and THC have the chemical formula of $C_{21}H_{30}O_2$. One of skill in the art will appreciate that for conversion of CBD to THC, the double bond 1202 is changed to a single bond and a new bond 1302 is created forming a six-member ring.

The bioactivity of molecule of THC is different within the human body when CBD is present, versus when CBD is not present. In particular, CBD activates bioreceptors in human cells which then allow molecules of THC into those cells. In other words, in the presence of molecules of CBD, THC is absorbed into a variety of human cells. In contrast, when the molecule of CBD is not present, the molecule of THC is not internalized by receptors into cells. Instead, it acts on the exterior of synapses, allowing them to fire more efficiently and increasing efficiency of neurotransmission. This is why THC has shown promise in treating diseases where neurotransmission has been impaired (such as Alzheimer's disease, Parkinson's disease, etc.). Thus, when the purpose of THC usage is to help with neurotransmission it is preferable that the amount of CBD is low (20% or lower). The method 1100 allows maximization of THC extraction without increasing CBD levels.

FIG. 11 shows that the method 1100 can include sorting 1102 the different parts of the plant. The different parts of a cannabis plant have different chemical properties and have compounds such as CBD and THC in different concentrations and at different stages of chemical creation, so sorting allows them to be extracted differently. To sort the parts of the plant, the cannabis plant is uprooted and washed. The plant is then mechanically comminuted (e.g., cutting or grinding) and the different plants are placed in different containers, which can be labeled (for example, with the part of the plant, the date of sorting, etc.).

The sorting table of FIG. 2 can be used for sorting, just as in FIG. 1 discussed above. In some embodiments, roots can be placed in the first opening 204, stems in the second opening 204, branches in the third opening 204, and flowers in the fourth opening 204. A series of baskets 206 are placed under the openings 204 to catch the sorted plant material. The different parts of a cannabis plant have different chemical properties and have compounds such as CBD and THC in different quantities and at different stages of chemical creation, so sorting allows them to be extracted differently as discussed above with respect to FIG. 3.

FIG. 11 shows that the method 1100 can also include shredding 1104 of the plant parts. Shredding 1104 (or mulching) is further comminution of the plant materials to create much smaller particles. Shredding 1104 does not change the volume of the plant materials but does change the surface area. In other words, by mechanically breaking up the plant matter, the surface area available for CBD and THC extraction is increased, decreasing the time needed for the extraction process. The shredded materials can be weighed and labeled similar to the above. Typically, once the amount of biomass is between 3 and 5 kilograms, the container is replaced with a new container, but the amount of biomass depends on the size of fermentation tanks (described below). The mulching can be done in mulching machine 400 as discussed above with respect to FIG. 4.

FIG. 11 additionally shows that the method 1100 can include adding 1106 fermentation materials to each container (which already includes shredded plant material). The fermentation materials depend on the desired final product. Exemplarily, rice will be used herein, which would result in infused rice wine, but other materials are contemplated herein, such as wine from grapes, wine from grains such as beans and peas, fruit wine, wine from aromatic plants such as garden flowers, carnations, poppies, roses, etc., beer, and other spirits. For the production of rice wine, the fermentation materials can include vegetable oil (~1.9 times the cannabis biomass by weight), sugar (~0.25 times the cannabis biomass by weight) and rice (~1.9 times the cannabis biomass by weight). Vegetable oils, or vegetable fats, are oils extracted from seeds or from other parts of fruits.

Soybean oil, grape seed oil, and cocoa butter are examples of seed oils or fats from seeds while olive oil, palm oil, and rice bran oil are examples of fats from other parts of fruits.

FIG. 11 moreover shows that the method 1100 can include placing 1108 the mixed components in fermentation tanks. Each different portion of the plant (e.g., root, stem leaves, flowers) is placed in different fermentation tanks. For example, in the fermentation system of FIG. 5, flowers are placed in first fermentation tank 502a, roots are placed in second fermentation tank 502b, stems are placed in third fermentation tank 502c, and branches and leaves are placed in further fermentation tank 502d. All of the biomass except the flowers is placed in second fermentation tank 502b, third fermentation tank 502c, and fourth fermentation tank 502d. This placement is critical to increase THC production and minimize CBD production, as described below. The difference in placement between FIG. 1 and FIG. 11 changes the final results of what is collected in terms of CBD and THC percentages.

FIG. 11 also shows that the method 1100 can include activating 1110 a yeast mixture. Activating 1110 the yeast mixture involves adding yeast to a water and sugar mixture which allows the yeast to begin growing and undergoing metabolic processes. Activated yeast begins to work faster than inactive or dry yeast. Activating 1110 a yeast mixture involves adding warm water (between 32° C. and 38° C. into storage tank 504). Then, sugar at a ratio of approximately 1 to 100 is added (1 kilogram of sugar for every 100 kilograms of water—1 liter of water weighs 1 kilogram) and yeast at a ratio of approximately 1 to 1000 is added (1 gram of yeast for every 1 kilogram of water). The sugar is a food source for the yeast and the warm water increases the speed of yeast metabolic processes. The water/sugar/yeast mixture is left alone for ~45 minutes to incubate within the storage tank 504.

FIG. 11 further shows that the method 1100 can include adding 1112 the activated yeast to the fermentation tanks (this is counted as day 0). This is done by having the valves 506b, 506c, 506d, 506e, 506f, 506g, and 506h of FIG. 5 open (valve 506i is closed) and then opening valve 506a, allowing the activated yeast mixture to flow into fermentation tanks 502 (the fluid level will not be high enough to flow into macerated oil tank 508). The cannabis biomass in each fermentation tank 502 is now suspended in the activated yeast mixture.

FIG. 11 moreover shows that the method 1100 includes leaving 1114 the mixtures in each alcoholic fermentation tank for 10 days to allow fermentation to proceed. Because storage tank 504 is the same volume as fermentation tanks 502, the activated yeast mixture will reach to approximately the bottom metallic screen filter 702b. However, because the biomass mixture includes oil (as part of the fermentation materials) there will be a water/oil interface at or near the bottom metallic screen filter 702b. The yeast can migrate through the interface and will equalize between the water and the vegetable oil, but the biomass will remain within the vegetable oil. After the volume equalizes in the fermentation tanks, valves 506a, 506b, 506c, 506d, 506e, 506f, and 506g are left open, allowing the fermentation products to mix throughout days 0-10. Valves 506h and 506i are both closed so that macerated oil and alcoholic fermenting rice wine remain within the fermentation tanks. One of skill in the art will appreciate that this configuration of open and closed valves is different than in method 100 of FIG. 1.

One of skill in the art will understand that leaving 1114 the alcoholic fermentation tanks 502 alone refers to the addition of other materials (such as additional biomass or activated yeast) but does not mean that samples and measurements cannot be taken. For example, on each day samples can be taken from each of the fermentation tanks 502. Samples can include 500 mL from each fermentation tank 502. The samples may be tested for pH, temperature, alcoholic %, High-Performance Liquid Chromatography (HPLC), etc. Examples of test results are shown in FIGS. 14, 15, 16, 17, and 18 (where FIG. 14 illustrates the percentage of various Cannabinoids (including CBD and THC) prior to transformation of CBD into THC, FIG. 15 illustrates the same results, but as a percentage within the fermented alcohol and macerated oil, FIG. 16 illustrates an example of a high performance liquid chromatography (HPLC) sample report of a sample extracted by the disclosed method showing percentage of CBD, CBDA, THC, and THCA, FIG. 17 illustrates an example of high performance liquid chromatography (HPLC) during the 21 days of fermentation, and FIG. 18 illustrates the HPLC results on day 21 including percentages of cannabinoids: CBDV, CBDVA, CBG, CBD, CBDA, CBGA, THCV, CBN, THC, CBC, and THCA). Over time, CBD is extracted where it remains in the vegetable oil carrier because it is hydrophobic. THC, on the other hand, is extracted and migrates into the water in the fermentation tanks because it is hydrophilic. However, the presence of proteins (enzymes) from the flowers covert the CBD within the oil into THC resulting in high percentages of THC and low percentages (less than 20 percent) of CBD. The proteins within the flower biomass convert the crystal CBD into THC, which then migrates into the water in the fermentation tanks, reducing the concentration of CBD in the macerated oil and increasing the concentration of THC in the water. Further, the rice is being fermented creating a rice wine which is infused with molecules of THC and a CBD macerated oil, further separating the molecules of CBD and THC.

FIG. 11 also shows that the method 1100 can include equalizing 1116 the alcoholic fermentation tanks throughout fermentation. Because the valves 506b, 506c, 506d, 506e, 506f, and 506g are open, the water/sugar/yeast portion of each of fermentation tanks 502 are allowed to mix with one another. Likewise, the macerated oil within fermentation tanks 502 are allowed to mix with one another. However, the water/sugar/yeast portions and macerated oil portions remain separated because one is hydrophilic and one is hydrophobic. Because each fermentation tank has different plant matter, the amounts of molecules CBD and THC will equalize continually due to diffusion while the valves 506b, 506c, 506d, 506e, 506f, and 506g are open.

FIG. 11 further shows that the method 1100 can include adding 1118 a sugar/water mixture to storage tank 504. Storage tank 504 is refilled with warm water. Sugar is added to the water in storage tank 504 at a rate of approximately 1 to 100 (1 kilogram of sugar for every 100 kilograms of water).

FIG. 11 additionally shows that the method 1100 can include adding 1120 $\frac{1}{10}^{th}$ of the sugar/water mixture to the first fermentation tank 502a through valve 506a each day of days 10-21. This raises the level of the water/oil interface in each tank (this interface would be at about half the height of each fermentation tank, except the presence of the biomass pushes this higher—closer to 75% of the height of the fermentation tanks). In addition, it raises the top level of the oil within the tank, so that the oil flows through valves 506b, 506d, 506f, and 506h into macerated oil tank 508.

FIG. 11 moreover shows that the method 1100 can include collecting 1122 the macerated oil on day 21. Macerated oils are vegetable oils to which other matter, such as herbs, has been added. Thus, the macerated oil is vegetable oil with molecules of CBD mixed into the oil. Step 1122 in FIG. 11 can include mixing the oil. Because different parts of the plant have different levels of CBD, mixing the oil during collection equalizes the CBD concentration throughout the oil. The step of collecting the macerated oil, as shown at step 1122 in FIG. 11, may also include closing valve 506*h* prior to mixing so that oil is not pushed back into fermentation tanks 502 during mixing. One of skill in the art will appreciate that because most CBD has been converted to THC and the remaining CBD is in the macerated oil, very little CBD will remain after collecting the macerated oil.

FIG. 11 also shows that the method 1100 can include collecting 1124 the infused alcohol on day 21. Collecting 1124 the infused alcohol includes opening valve 506*i*. Because valves 506*c*, 506*e*, and 506*g* are opened but valves 506*b*, 506*d*, 506*f*, and 506*h* are closed, any liquid now flows into infused alcohol tank 510 through valve 506*i*. Because the macerated oil has been removed, the remaining liquid is THC infused alcohol (in this example, rice wine).

The concentrations of CBD in the macerated oil and oil of THC in the infused rice wine can be calculated using the following equations:

$$[CBD] = \frac{\log\left(\frac{V(\text{Passive})}{V(\text{Total})} * \% \text{ Alcohol(final)} * \text{pH(final)} * \frac{\text{Temperature (° C.)}}{\text{number of fermentaion days}}\right)}{\cos\left(\frac{m(\text{BM})}{m(\text{vegetal oil})} - \frac{m(\text{sugar})}{m(\text{rice})}\right)}$$

$$[THC] = \frac{[CBD]}{[\% \text{ Alcohol(final)}] * [\% \text{ Alcohol(final)}]}$$

$$\% [CBD] = [CBD] * 100$$

$$\% [THC] = [THC] * 100$$

$$\text{if, } X = \frac{[THC] + [CBN]}{[CBD]}; \text{ and } [CBN] = 0$$

$$X = \frac{1}{[\% \text{ Alcohol(final)}] \wedge 2}$$

These concentrations are significantly higher than concentrations obtained using conventional methods.

"Exemplary" is used herein to mean "serving as an example, instance, or illustration." Any aspect described in this document as "exemplary" is not necessarily to be construed as preferred or advantageous over other aspects.

Throughout the drawings, like reference characters are used to designate like elements. As used herein, the term "coupled" or "coupling" may indicate a connection. The connection may be a direct or an indirect connection between one or more items. Further, the term "set" as used herein may denote one or more of any items, so a "set of items" may indicate the presence of only one item or may indicate more items. Thus, the term "set" may be equivalent to "one or more" as used herein.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention.

The embodiments were chosen and described in order to best explain the principles of the invention and the practical application, and to enable others of ordinary skill in the art to understand the invention for various embodiments with various modifications as are suited to the particular use contemplated. The present invention according to one or more embodiments described in the present description may be practiced with modification and alteration within the spirit and scope of the appended claims. Thus, the description is to be regarded as illustrative instead of restrictive of the present invention.

What is claimed is:

1. A method for extracting Tetrahydrocannabinol from cannabis plants, the method comprising:
   sorting different parts of cannabis plants, wherein the different parts of the cannabis plants include at least flowers;
   shredding each of the different parts of the cannabis plants and placing each of the different parts of the cannabis plants in a separate container;
   mixing fermentation materials with each of the different parts of the cannabis plants;
   placing the mixed components in a set of fermentation tanks, wherein the each of the different parts of the cannabis plants is placed in a separate fermentation tank;
   wherein each fermentation tank:
      includes a pair of screen filters;
      is connected to at least one of the other fermentation tanks in the set of fermentation tanks at a location above the pair of screen filters; and
      is connected to at least one of the other fermentation tanks in the set of fermentation tanks at a location below the pair of screen filters;
   activating a yeast mixture;
   adding the activated yeast mixture to the fermentation tanks on day 0;
   leaving the mixtures in each fermentation tank for 10 days to allow fermentation to proceed;
   equalizing the mixtures in each of the fermentation tanks on days 0 through 10 by opening connections between the fermentation tanks;
   creating a water/sugar mixture and adding $\frac{1}{10}^{th}$ of the water/sugar mixture to the fermentation tanks each day for 10 days;
   collecting a macerated oil on day 21 by allowing the macerated oil to flow to an oil collection tank; and
   collecting an infused alcohol on day 21 after collecting the macerated oil by allowing the infused alcohol to flow to an alcohol collection tank.

2. The method of claim 1, wherein the different parts of the cannabis plants include:
   roots;
   stems;
   branches; and
   flowers.

3. The method of claim 1, wherein the fermentation materials include an oil.

4. The method of claim 3, wherein an amount of oil added to each separate container is approximately 1.9 times the different parts of the cannabis plants by weight.

5. The method of claim 3, wherein the oil includes at least one of:
   soybean oil grape seed oil
cocoa butter
olive oil
palm oil; or
rice bran oil.

6. The method of claim 1, wherein the fermentation materials include sugar.

7. The method of claim 6, wherein an amount of sugar added to each separate container is approximately 0.25 times the different parts of the cannabis plants by weight.

8. The method of claim 1, wherein the fermentation materials include a fermentable substance.

9. The method of claim 8, wherein an amount of fermentable substance added to each separate container is approximately 1.9 times the different parts of the cannabis plants by weight.

10. The method of claim 8, wherein the fermentable substance includes at least one of:
grapes;
grains;
fruit
aromatic plants;
beer; or
spirits.

11. A method for extracting THC Tetrahydrocannabinol from cannabis plants, the method comprising:
sorting different parts of a plant, wherein the different parts of the plant include:
roots;
stems;
branches; and
flowers;
shredding each of the different parts of the plant and placing each different parts of the plant in a separate container;
adding fermentation materials to each separate container, wherein the fermentation materials include:
vegetable oil;
sugar; and
rice;
placing the mixed components in fermentation tanks, wherein:
the flowers are placed in a first fermentation tank; and
the roots, stems, branches, and leaves are placed in a second fermentation tank, a third fermentation tank, and a fourth fermentation tank;
wherein each fermentation tank:
includes a pair of metallic screen filters;
is connected to the other fermentation tanks at a location above the pair of metallic screen filters; and
is connected to the other fermentation tanks at a location below the pair of metallic screen filters;
activating a yeast mixture;
adding the activated yeast mixture to the fermentation tanks on day 0;
leaving the mixtures in each fermentation tank for 10 days to allow fermentation to proceed;
equalizing the mixtures in each of the fermentation tanks on days 0 through 10 by opening the connections between fermentation tanks;
creating a water/sugar mixture and adding $1/10^{th}$ of water/sugar mixture to the fermentation tanks each day on days 10-19;
collecting a macerated oil on day 21 by allowing the macerated oil to flow to an oil collection tank; and
collecting an infused alcohol on day 21 after collecting the macerated oil by allowing the infused alcohol to flow to an alcohol collection tank.

12. The method of claim 11, wherein:
a first metallic screen filter of the pair of metallic screen filters in each of the fermentation tanks is located approximately 25% of total height of the fermentation tank from a top of the fermentation tank; and
a second screen filter of the pair of metallic screen filters in each of the fermentation tanks is located approximately 25% of the total height of the fermentation tank from a bottom of the fermentation tank.

13. The method of claim 11, wherein activating the yeast mixture includes:
adding yeast to water, wherein an amount of yeast is approximately 0.001 of an amount of water by weight; and
adding sugar to the water, wherein an amount of sugar is approximately 0.01 of the amount of water by weight.

14. The method of claim 11, wherein:
an amount of sugar in the sugar/water mixture is approximately 0.01 an amount of water by weight.

15. The method of claim 11 further comprising:
testing the macerated oil in each fermentation tank in days 10-21.

16. A system for extracting Tetrahydrocannabinol from cannabis plants, the system comprising:
a first fermentation tank, the first fermentation tank:
includes:
a first screen filter, wherein the first screen filter is located approximately 25% of total height of the first fermentation tank from the top of the first fermentation tank; and
a second screen filter, wherein the second screen filter in the pair of metallic screen filters is located approximately 25% of total height of the first fermentation tank from the bottom of the first fermentation tank; and
is configured to receive the flowers of cannabis plants between the first screen filter and the second screen filter;
a second fermentation tank, the second fermentation tank:
includes:
a first screen filter, wherein the first screen filter is located approximately 25% of total height of the second fermentation tank from the top of the second fermentation tank; and
a second screen filter, wherein the second screen filter in the pair of metallic screen filters is located approximately 25% of total height of the second fermentation tank from the bottom of the second fermentation tank;
a first connection to the first fermentation tank above the first screen filter;
a second connection to the first fermentation tank below the second screen filter; and
is configured to receive the roots, stems, branches, and leaves of the cannabis plants between the first screen filter and the second screen filter;
a third fermentation tank, the third fermentation tank:
includes:
a first screen filter, wherein the first screen filter is located approximately 25% of total height of the third fermentation tank from the top of the third fermentation tank; and
a second screen filter, wherein the second screen filter in the pair of metallic screen filters is located approximately 25% of total height of the third fermentation tank from the bottom of the third fermentation tank;
a first connection to the first fermentation tank above the first screen filter;
a second connection to the first fermentation tank below the second screen filter; and
is configured to receive the roots, stems, branches, and leaves of the cannabis plants between the first screen filter and the third screen filter;
a fourth fermentation tank, the fourth fermentation tank: includes:
a first screen filter, wherein the first screen filter is located approximately 25% of total height of the fourth fermentation tank from the top of the fourth fermentation tank; and
a second screen filter, wherein the second screen filter in the pair of metallic screen filters is located approximately 25% of total height of the fourth fermentation tank from the bottom of the fourth fermentation tank;
a first connection to the first fermentation tank above the first screen filter;
a second connection to the first fermentation tank below the second screen filter; and
is configured to receive the roots, stems, branches, and leaves of the cannabis plants between the first screen filter and the fourth screen filter;
a storage tank, wherein the storage tank includes a connection to the first fermentation tank;
a macerated oil tank, wherein the macerated oil tank includes a connection to the fourth fermentation tank above the first screen filter of the fourth fermentation tank; and
an infused alcohol tank, wherein the infused alcohol tank includes a connection the to the fourth fermentation tank below the second screen filter of the fourth fermentation tank.

17. The system of claim 16 further comprising:
one or more supports in the first fermentation tank above the first screen filter;
one or more supports in the first fermentation tank below the second screen filter;
one or more supports in the second fermentation tank above the first screen filter;
one or more supports in the second fermentation tank below the second screen filter;
one or more supports in the third fermentation tank above the first screen filter;
one or more supports in the third fermentation tank below the second screen filter;
one or more supports in the fourth fermentation tank above the first screen filter; and
one or more supports in the fourth fermentation tank below the second screen filter.

18. The system of claim 16 wherein each connection includes a valve.

19. The system of claim 16 wherein each fermentation tank is made of food grade steel.

20. The system of claim 16 wherein each fermentation tank is made of wood.

* * * * *